US009005201B2

(12) United States Patent
Munro et al.

(10) Patent No.: US 9,005,201 B2
(45) Date of Patent: Apr. 14, 2015

(54) INTRAMEDULLARY ROD WITH VENT

(75) Inventors: Chad Munro, Nova Scotia (CA); Peter Blanchard, Prince Edward Island (CA); Nick McGrath, Nova Scotia (CA); Matthew Terauds, Nova Scotia (CA); Leanna Maclean, Nova Scotia (CA); Sam Veres, Nova Scotia (CA)

(73) Assignee: Halifax Biomedical Inc., Mabou, Nova Scotia (CA)

( * ) Notice: Subject to any disclaimer, the term of this patent is extended or adjusted under 35 U.S.C. 154(b) by 739 days.

(21) Appl. No.: 12/296,255

(22) PCT Filed: Apr. 5, 2007

(86) PCT No.: PCT/CA2007/000567
§ 371 (c)(1),
(2), (4) Date: Jan. 6, 2010

(87) PCT Pub. No.: WO2007/112589
PCT Pub. Date: Oct. 11, 2007

(65) Prior Publication Data
US 2010/0137863 A1 Jun. 3, 2010

Related U.S. Application Data

(60) Provisional application No. 60/789,571, filed on Apr. 6, 2006.

(51) Int. Cl.
| | |
|---|---|
| *A61B 17/56* | (2006.01) |
| *A61B 17/72* | (2006.01) |
| *A61B 17/74* | (2006.01) |
| *A61B 17/88* | (2006.01) |
| *A61B 19/00* | (2006.01) |

(52) U.S. Cl.
CPC .......... *A61B 17/7233* (2013.01); *A61B 17/7208* (2013.01); *A61B 17/725* (2013.01); *A61B 17/744* (2013.01); *A61B 17/8872* (2013.01); *A61B 2019/302* (2013.01)

(58) Field of Classification Search
CPC ............... A61B 17/72; A61B 17/7241; A61B 17/7283; A61B 17/7233
USPC ....................................................... 606/62–68
See application file for complete search history.

(56) References Cited

U.S. PATENT DOCUMENTS

| | | | | |
|---|---|---|---|---|
| 3,076,453 | A | * | 2/1963 | Tronzo ............................ 606/67 |
| 3,255,747 | A | * | 6/1966 | Di Cosola et al. .............. 606/80 |
| 6,183,470 | B1 | * | 2/2001 | Booth et al. ..................... 606/53 |
| 6,443,954 | B1 | * | 9/2002 | Bramlet et al. ................. 606/62 |
| 6,488,684 | B2 | * | 12/2002 | Bramlet et al. ................. 606/62 |
| 6,648,889 | B2 | * | 11/2003 | Bramlet et al. ................. 606/62 |

(Continued)

FOREIGN PATENT DOCUMENTS

| | | |
|---|---|---|
| CA | 2500864 | 4/2004 |
| CA | 2529607 | 12/2004 |

(Continued)

*Primary Examiner* — Ellen C Hammond
*Assistant Examiner* — Stuart S Bray
(74) *Attorney, Agent, or Firm* — Gowling Lafleur Henderson LLP

(57) ABSTRACT

The invention relates to a device for providing skeletal support. A bone support device comprising an upright rod having a proximal and a distal end; at least one support member located near the proximal end for securing the rod to the bone; at least one distal anchoring element; and a vent member is provided.

5 Claims, 7 Drawing Sheets

(56) References Cited

U.S. PATENT DOCUMENTS

| | | | |
|---|---|---|---|
| 6,863,670 B2* | 3/2005 | Zheng et al. | 606/64 |
| 7,160,302 B2* | 1/2007 | Warburton | 606/62 |
| 7,488,320 B2* | 2/2009 | Middleton | 606/62 |
| 7,967,820 B2* | 6/2011 | Bonutti et al. | 606/64 |
| 8,308,726 B2* | 11/2012 | Kumar et al. | 606/67 |
| 8,545,499 B2* | 10/2013 | Lozier et al. | 606/63 |
| 2002/0156473 A1* | 10/2002 | Bramlet et al. | 606/62 |
| 2002/0161369 A1* | 10/2002 | Bramlet et al. | 606/67 |
| 2003/0083662 A1* | 5/2003 | Middleton | 606/72 |
| 2003/0195515 A1* | 10/2003 | Sohngen | 606/62 |
| 2005/0015061 A1* | 1/2005 | Sweeney | 604/264 |
| 2006/0106386 A1* | 5/2006 | Reber et al. | 606/65 |
| 2006/0142763 A1* | 6/2006 | Munro et al. | 606/62 |
| 2006/0149247 A1* | 7/2006 | Frigg et al. | 606/64 |
| 2006/0200141 A1* | 9/2006 | Janna et al. | 606/62 |
| 2006/0241604 A1* | 10/2006 | Frigg et al. | 606/62 |
| 2007/0049938 A1* | 3/2007 | Wallace et al. | 606/62 |
| 2007/0049939 A1* | 3/2007 | Wallace et al. | 606/62 |
| 2007/0049940 A1* | 3/2007 | Wallace et al. | 606/62 |
| 2007/0123876 A1* | 5/2007 | Czartoski et al. | 606/62 |
| 2007/0260248 A1* | 11/2007 | Tipirneni | 606/65 |
| 2008/0021474 A1* | 1/2008 | Bonutti et al. | 606/64 |
| 2008/0033436 A1* | 2/2008 | Song et al. | 606/61 |
| 2008/0051790 A1* | 2/2008 | Defossez | 606/64 |
| 2008/0108996 A1* | 5/2008 | Padget et al. | 606/67 |
| 2008/0275566 A1* | 11/2008 | Lewis et al. | 623/20.34 |
| 2008/0294164 A1* | 11/2008 | Frank et al. | 606/64 |
| 2009/0069813 A1* | 3/2009 | von Hoffmann et al. | 606/65 |
| 2009/0125028 A1* | 5/2009 | Teisen et al. | 606/63 |
| 2009/0177200 A1* | 7/2009 | Saab et al. | 606/63 |
| 2009/0204117 A1* | 8/2009 | Middleton | 606/62 |
| 2011/0077651 A1* | 3/2011 | Lozier et al. | 606/62 |
| 2011/0295253 A1* | 12/2011 | Bonutti et al. | 606/62 |

FOREIGN PATENT DOCUMENTS

| | | |
|---|---|---|
| CA | 2531541 | 12/2004 |
| DE | 20105775 | 6/2001 |
| WO | 00/27298 | 5/2000 |
| WO | 2004/030550 | 4/2004 |

* cited by examiner

INTRAMEDULLARY ROD WITH VENT

CROSS-REFERENCE TO RELATED APPLICATIONS

This application is the National Stage of International Application No. PCT/CA2007/000567 filed Apr. 5, 2007, which claims the priority of U.S. Application No. 60/789,571, filed on Apr. 6, 2006. The contents of both applications are hereby incorporated by reference in their entirety.

FIELD OF INVENTION

The present invention relates to a bone support system, particularly an intramedullary rod for long bones that is especially useful for patients with cancer in the bone.

BACKGROUND OF THE INVENTION

The need for bone implants is increasing due to accidents, genetic defects, osteoporosis and cancer. This need is expected to expand as the number of older people in the population increases dramatically in the next two decades. In addition, new therapies are allowing patients with cancer to live longer.

Intramedullar nails or rods are implantable devices that are inserted into the medullary canal of long bones to provide support. A typical intramedullary nail comprises a rod. At the head of the rod there is a hole transverse to the longitudinal axis of the rod. A means for anchoring the rod, such as a screw is passed through the hole to fasten the rod to the bone. The nails or rods are placed into the medullary canal through a hole that is drilled at one end of the bone.

There have been many attempts to provide improved intramedullary nails. For example, U.S. Pat. No. 6,443,954 discloses an intramedullary system for securing portions of a bone together has a lag screw assembly extending through a radial bore in an intramedullary nail. The lag screw is inserted into one portion of a bone and deployed to fix the leading end. The intramedullary nail is placed in the intramedullary canal of a portion of the bone and the trailing end of the lag screw assembly is adjustably fixed in the radial bore to provide compression between the lag screw assembly and the intramedullary nail. The intramedullary nail has a cap screw in the proximal end holding the lag screw assembly and a tang in the distal end. The tang has legs extending through the nail to fix the distal end in the intramedullary canal.

U.S. Pat. No. 6,527,775 discloses methods and devices for treating fractures in or adjacent the wrist and distal forearm employ an intramedullary interlocking fixation rod (i.e., it interlocks the distal and proximal fracture fragments together) to stabilize the skeletal structure in a manner which can inhibit the amount of collapse or loss in skeletal length exhibited by a patient with a distal radius fracture.

U.S. Pat. No. 6,755,862 describes an intramedullary strut in the form of nested telescopic members. The strut can be telescopically extended into the medullary canal to provide support.

An ideal permanent bone implant would be compatible with living tissue, easy to insert and be able to withstand the stresses typically placed upon bones during normal moment. For cancer patients, it is also desirable to have an implant that prevents the build-up of pressure in the medullary canal that can promote the dissemination of metastatic cells. It would also be desirable to have an implant that bears the full load to which the bone is normally subjected. However, it has proven difficult to develop an implant having all these features.

SUMMARY OF THE INVENTION

The invention relates to an improved intramedullary rod support system. The device of the invention is particularly useful for the treatment of cancerous bone although it can also be used to provide support to fractured bones or bones weakened by osteoporosis.

According to an aspect of the present invention there is provided an intramedullary rod that includes a vent feature. The vent maintains negative pressure in the medullary cavity. The vent can also be used to deliver or remove fluids.

In a preferred embodiment, the rod includes a thread portion that can secure the support assembly. The tensile element with threads allows for the use of larger elements that provide a better hold. It also provides increased strength and therefore a longer lifespan for the implant. In addition, this element reduces sliding for greater stability.

The present invention addresses the need for an improved bone support system, particularly one that is suitable for use in cancer patients.

In one aspect of the invention, there is provided a bone support device comprising:
  i. an upright rod having a proximal and a distal end;
  ii. at least one support member located near the proximal end for securing the rod to the bone;
  iii. at least one distal anchoring element; and
  iv. a vent member.

In a preferred embodiment, the vent member comprises an element having a through hole along its longitudinal axis.

In another preferred embodiment, the vent member comprises a channel through the longitudinal axis of the anchoring element.

In yet another preferred embodiment, the rod comprises a threaded opening at the proximal end adapted to receive the support member.

In a further preferred embodiment, the support member has a diameter larger than the rod.

In another preferred embodiment, the support member comprises an end cap.

In another preferred embodiment, the support member comprises an oblique hole across its longitudinal axis.

In another preferred embodiment, the bone support device further comprises a securement member in the oblique hole.

The securement member is a bolt in one preferred embodiment.

In a further preferred embodiment, the device is coated with an antimicrobial agent.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

The following description is of a preferred embodiment.

The present invention provides a novel bone support system. The bone support system typically comprises an intramedullary (IM) rod, one or more support elements, a cap section for the intramedullary rod, one or more bolt elements, and a venting element. It is apparent that functionally equivalent parts can be used. For example, the cap section can be a separate element or it may be integral with the rod. The venting element can be placed before or at the time of IM canal opening, IM canal preparation or IM rod insertion into the IM canal. The vent element allows for the application of negative pressure to the IM canal during those phases of the operation that would normally result in an increase in IM pressure. In addition, the vent element acts as a delivery channel for fluid, or there may be a separate channel (not shown) that is connected to the IM canal to allow for the delivery of fluids into the IM canal to aid in the removal or flushing of biological exudates. The IM rod is preferably fixed into the bone in a manner whereby no force, circumferential or longitudinal or otherwise, is transmitted to the bone between the proximal and distal support elements of the IM rod. The support elements of the bone support system (including the IM rod) are designed to provide better securement to the bone as compared to the prior art. This is due to the use of sizes, geometries, and configurations that are unattainable with the conventional IM rod bone support systems. The support elements may also include a conduit for the delivery of a bone cement like substance to augment the area surrounding the fixation elements. The differences in size, geometries and configurations also increase the lifespan of the device thereby reducing the risk of a break and the need for a secondary operation. In a preferred embodiment, the implantable portions of the bone support system have a coating that is antiseptic or antibiotic in nature.

Figure 1:
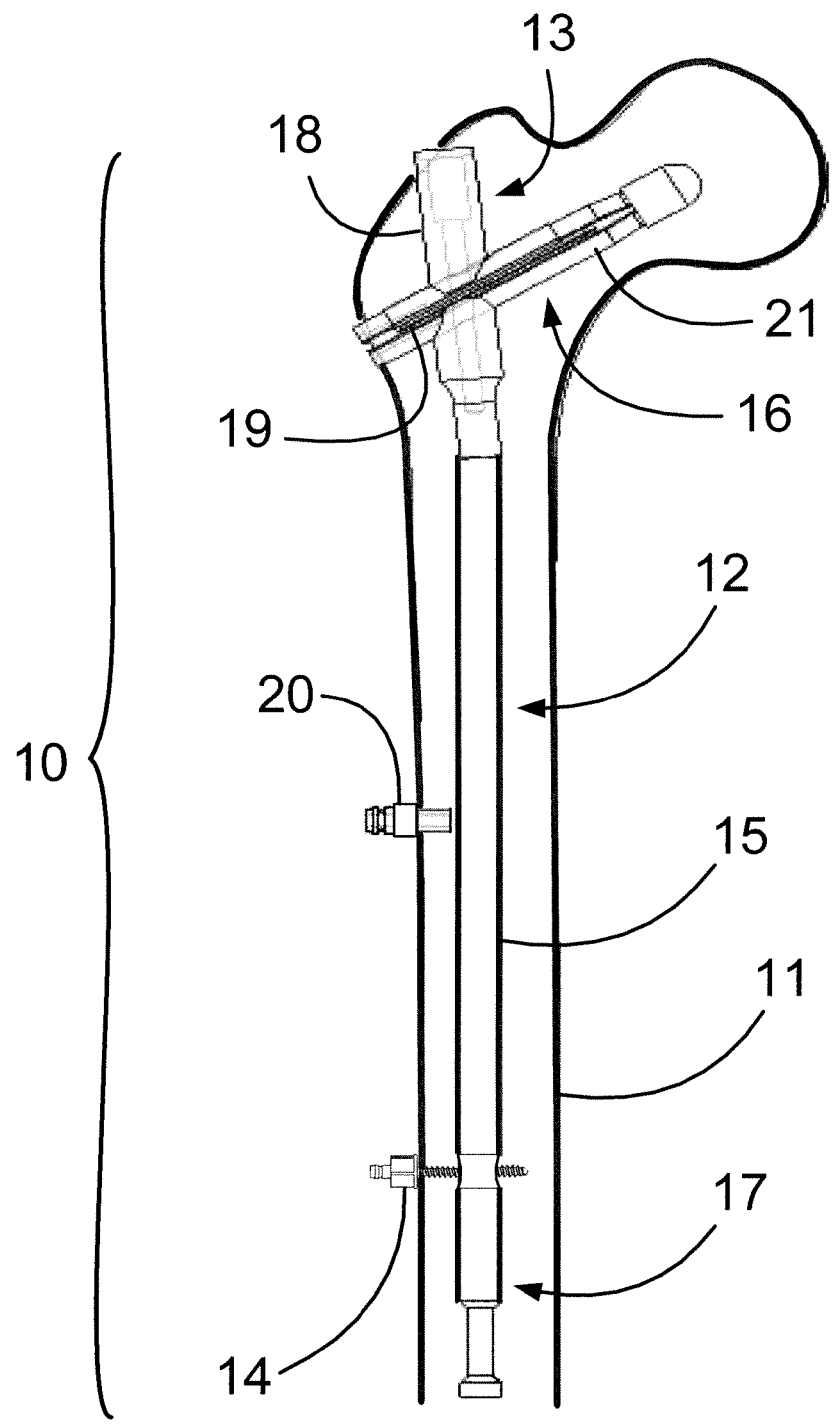
FIG. 1 shows a bone support system in accordance with an embodiment of the present invention.

Referring now to the figures, FIG. 1 illustrates a bone support system 10 according to the present invention. The bone support system 10 comprises an IM upright rod 12 having a proximal head 13, a shaft 15, and a distal end 17. An anchoring element 14, such as a locking bolt, nail or screw, transverses the rod near the distal end. A support element assembly 16 is associated with proximal head 13 of the rod. The support element assembly 16 may comprise one or more components. Typically, the support element assembly 16 includes a threaded securing member 19 to secure the head of the device in the femoral head and a sleeve or rod 21 that transects the IM upright rod 12 at an oblique angle. An end cap 18 is at the proximal end of the rod. The end cap may be a separate piece or part of the IM upright rod 12. The device also comprises a vent element 20 passing through the outside of the bone 11.

Figure 2:
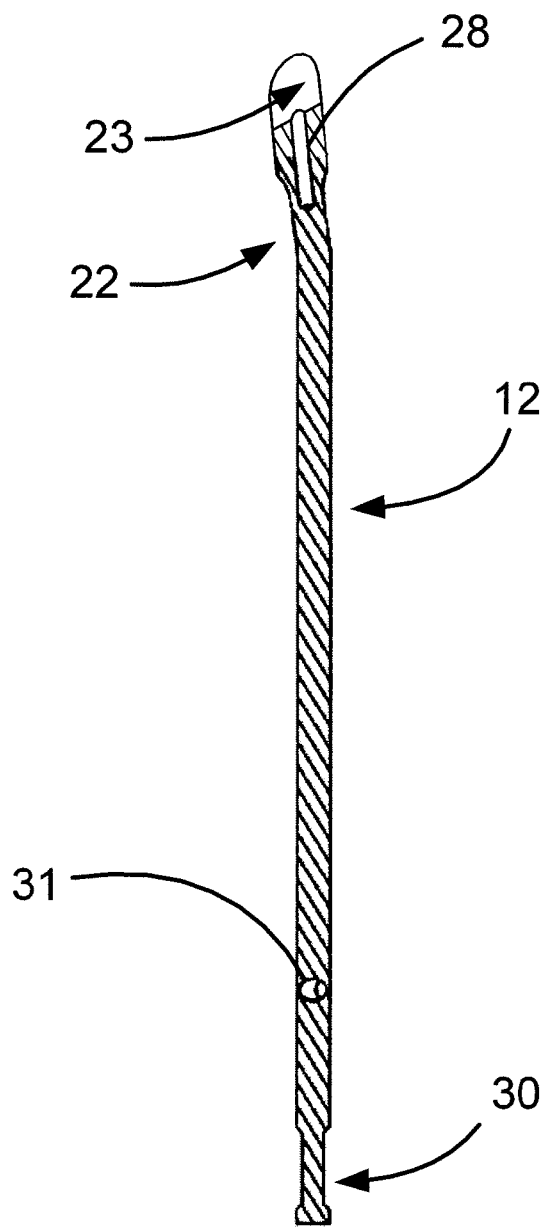
FIG. 2 shows an embodiment of an intramedullary rod for use in the system of FIG. 1.

FIG. 2 illustrates the IM upright rod 12 shown separately. The IM upright rod 12 has several distinct features including one or more bends 22 and at least one hole 23. The hole is preferably oriented at an oblique angle. The hole typically has a diameter that is larger than the IM rod, thereby creating an oblique round surface at the end of the IM rod. Furthermore the IM rod could have geometry that would interface with the support element assembly, and would have a hole and thread at one end 28 to receive a locking bolt. As well the IM rod could have geometry at the end portions 30 to allow for better hold within the bone. Finally the IM upright rod 12 may contain one or more holes 31 at an oblique or perpendicular angle to the long axis of the rod for the purpose of interfacing with a locking bolt or support element or a vent element.

Figure 3:
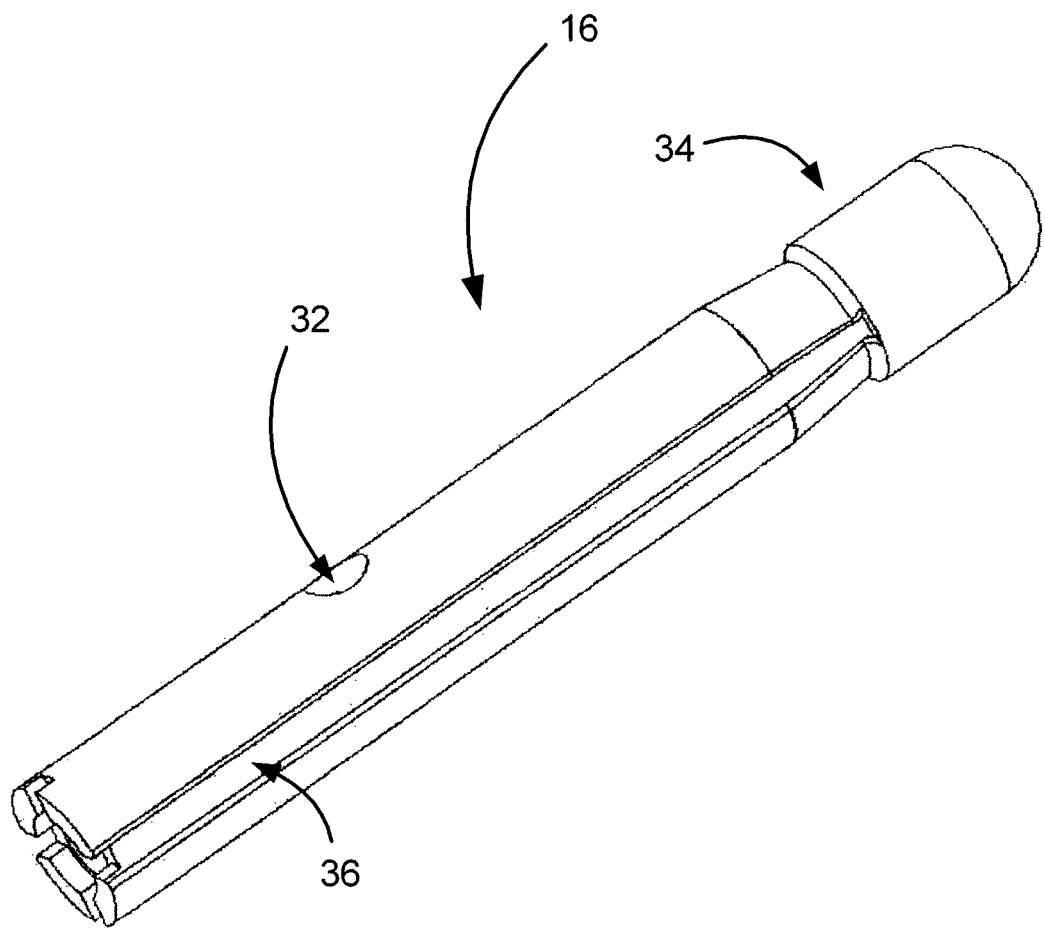
FIG. 3 illustrates an embodiment of a support screw for use in the system of FIG. 1.

The support element assembly 16 could be a combination of one or more support elements. FIG. 3 depicts a support screw or spiral blade or blade that has an oblique hole or oval or elongated hole 32 through which a locking bolt may pass. The support element assembly 16 has a portion 34 for resisting forces from the bone. The support element assembly 16 may also have a geometry or a slot 36 that runs axially on the outer surface of the support element assembly 16 to interact with another support element.

Figure 4:
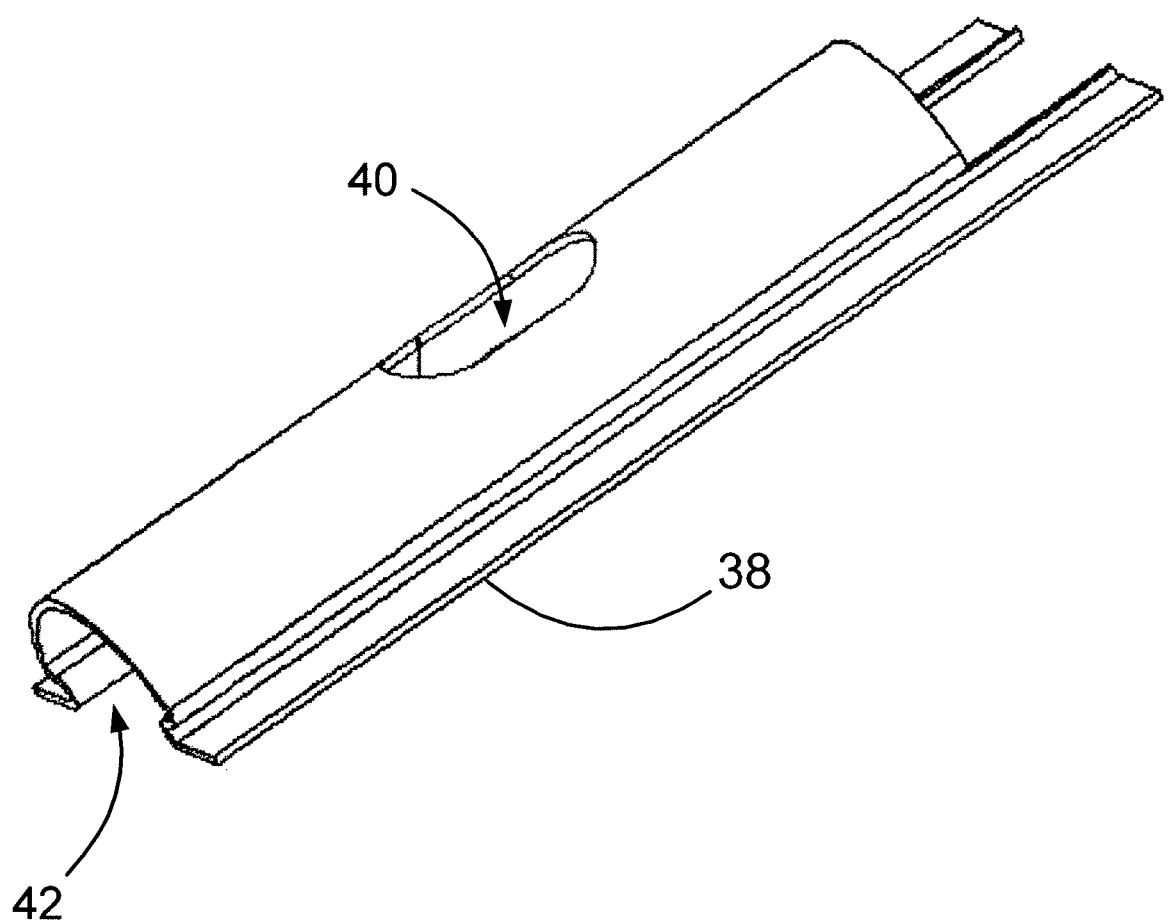
FIG. 4 illustrates an embodiment of a support element.

FIG. 4 depicts a possible support element that might interface with an element as shown in FIG. 3. This support element has a ridge that provides flexibility for resistance to bone forces 38. The support element also has an oblique hole or oval or elongated hole 40. The support element has a configuration 42 that allows it to interface with other support elements to allow for force transfer.

Figure 5:
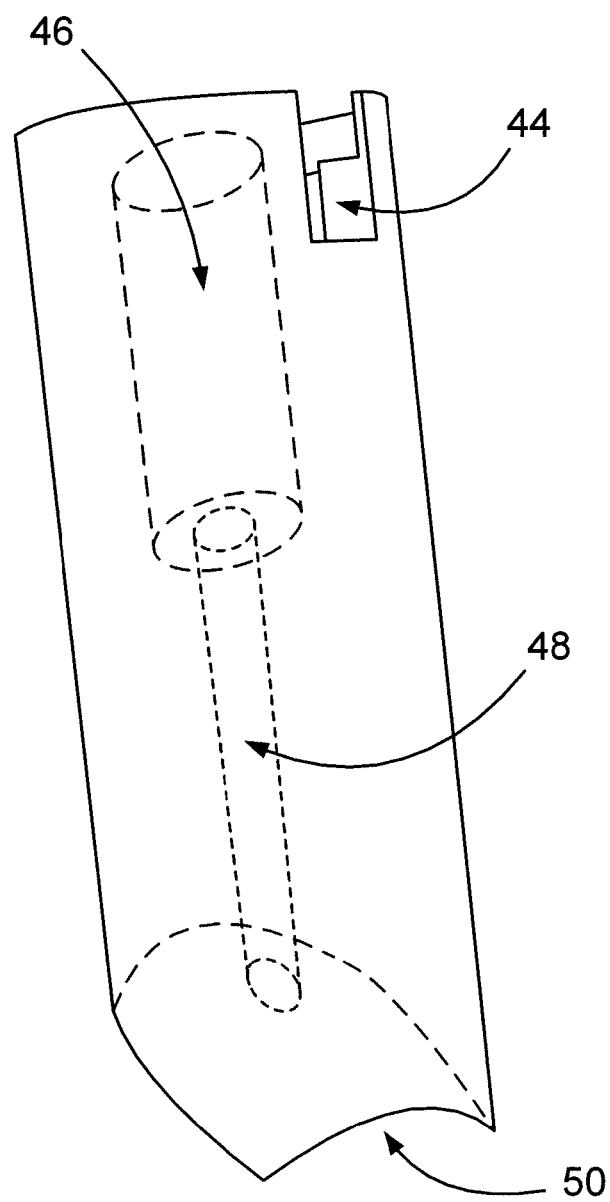
FIG. 5 illustrates an embodiment of a cap portion.

FIG. 5 depicts an IM cap section that would be required for the situation where the support element diameter is larger than the IM rod diameter at the point where the support element passes through device. This IM cap has a configuration 44 that allows for alignment with insertion instrumentation, and also has a thread at one end 46 for connection to an insertion instrumentation. A through hole is typically positioned along its long axis 48 such that a locking bolt can secure the IM cap and the support system assembly and the IM rod together using a thread that is located in the IM rod. Finally the IM cap has an oblique surface 50 that mirrors the oblique surface of the IM rod to interface with the support element assembly.

Figure 6:
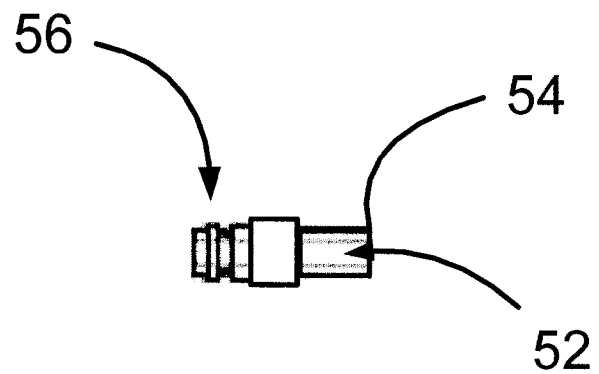
FIG. 6 shows an embodiment of a vent element.

FIG. 6 depicts a vent element consisting of a through hole along it long axis 52 means for fixation in the bone is located at one end 54, and the other end 56 comprises means for accepting the attachment of a suction tube or for the transmission of rotational forces or both.

Figure 7:
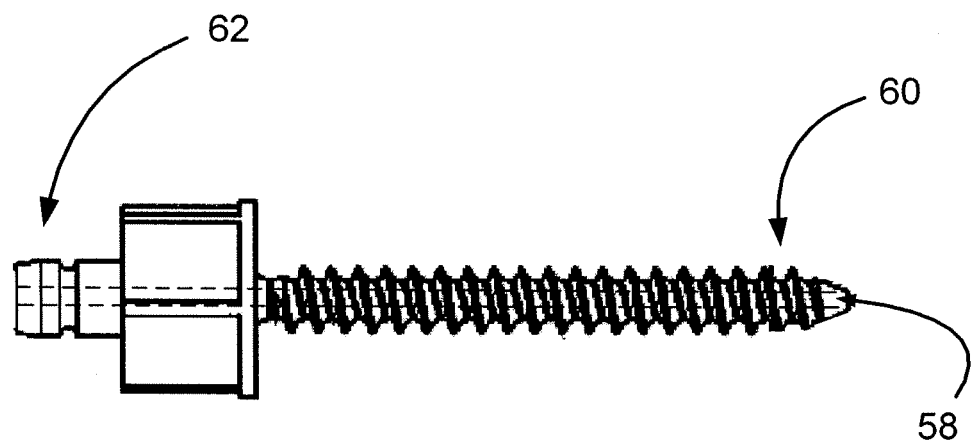
FIG. 7 illustrates an embodiment of a locking bolt.

FIG. 7 depicts a locking bolt element that may or may not include at least one through-hole along it longitudinal axis 58, means at one end 60 for fixation in the bone or in the IM rod, and means at the other end 62 for accepting the attachment of a suction tube or a geometry for the transmission of rotational forces or both. The locking bolt and the vent element may have the same or different designs.

The invention and it components can be produced using conventional machining and forming technologies. Additional production technologies may be included, for example, to allow for the addition of non-conventional elements such as antiseptic or antibiotic coatings.

The use of the device of the invention is now described.

The fracture is first repositioned to align fracture elements. Next an incision near the distal end of the bone would be made. A hole would be drilled and a vent would be screwed into place. Suction would be attached to the other end of the vent and a negative pressure would be continuously applied.

The proximal portion of the bone is then drilled out with a large drill bit to make a channel for the IM rod. After the drilling it may be advantageous to flush out the IM canal to remove the cancer cells. A brush may also be introduced to free cancer cells during the irrigation process. Next the canal would be reamed to a larger diameter along the bone shaft. This would ensure that there are not any pressure points on the bones, lowering the risk of secondary fracture but also reducing the pain of the patient. During or after the reaming process the canal might be irrigated where the vent would be used to remove the irrigation fluid and cells.

The guide wire is then introduced into the canal. The IM rod would be cannulated and pass subsequently over the guide wire. Cement may be introduced before the introduction of the IM rod via the vent, or it may be introduced during or after the introduction of the IM rod via the cannulation of the IM rod. The distal portion of the IM rod would be then fixed using a locking bolt through a distal hole in the IM rod.

Next an opening is created for the support elements on the lateral side of the bone, and then the support elements would be introduced. The support elements contact the IM nail in such a way as to indicate when the proper depth and rotational orientation of the support elements is reached. Once the support elements are in place the IM cap is introduced through the proximal opening and locked with a locking bolt, which would compress the IM cap the support elements and IM rod together.

This device is designed particularly for a patient with advanced cancer within the bone. The present invention has several advantages over prior devices. For example, it is the first device that includes a vent to ensure negative IM pressure. With prior devices, positive pressure is created in the IM cavity while it is being reamed and during nail insertion. This is a significant problem because the bone is porous and there are veins that enter the bones through these pores. In addition, bone cancer can lead to porous lesions. A positive IM pressure can cause the cancer cells, which inhabit the bone marrow and fat molecules located in this cavity to be forced outwards into these veins and consequently into the patients bloodstream. Cancer cells reintroduced into the blood stream can cause further metastasis, and fat globules can result in fat embolism. Fat embolism results when fat molecules block blood passages that can lead to serious health problems and even cardiac arrest.

Another advantage of the present invention is that the IM rod is threaded near the proximal end to interact with a locking bolt to secure IM cap, support assembly and IM rod construct. Because the rod is threaded, it can connect to a support element that is larger than that normally associated with that size rod. The support assembly can therefore have dimensions larger than the IM rod. Because the support assembly is larger, it can provide a better hold and a longer life. A locking bolt (a tensile element) with threads allows larger support elements that in turn provide for better hold to a poor bone structure. There is increased strength due to larger elements and therefore greater lifespan of the implant. In addition, sliding is reduced due to the compression of all of the support elements between the IM rod and cap.

A further advantage is that there is no load sharing with the bone when the present invention is used. All other devices are designed to load share with the bone to encourage strengthening and healing of the bone. Pathological fractures of the femur resulting from metastatic cancer need to be treated differently than normal fractures since the bone composition has changed drastically due to the cancerous activity. When treating non-cancerous fractures, implant/bone load sharing is usually employed because it promotes healing and bone growth. Since, loading a metastatic or fractured bone is extremely painful, load sharing is unacceptable in patients with bone cancer, as these patients' bones will not heal. An implant for these patients must bear the full load to which the femur is subjected.

By using the present invention, the implant surgery remains minimally invasive. This is important since the patient's general health condition is already fragile and a fast recovery time is desired. Also, with the decreased bone integrity, fixation techniques require proper anatomical fit to avoid creating pressure points that can develop into secondary fractures.

Another advantage of the present invention is that the components can be coated with an antibiotic or antiseptic composition to reduce the chances of deep infection.

It will be appreciated that while specific embodiments have been described for use in a femur, the present invention can be adapted for use in other long bones. Likewise, while specific reference has been made to the use of the device in patients with bone cancer, the device and method of the invention can be applied to other conditions that require bone support.

The above description and the drawings are illustrative of a preferred embodiment of the invention. It is not intended that the present invention be limited to the illustrated embodiments. Modifications and substitutions of equivalents are intended to be included within the scope of the invention.

The invention claimed is:

1. A bone support device for installation into a subject's femur, comprising:
   i. an intramedullary upright rod having a proximal end, a shaft, and a distal end;
   ii. a support element assembly engaging with the intramedullary upright rod at the proximal end, said support element assembly securable to the intramedullary upright rod with an end cap, said support element assembly having a larger diameter than the diameter of the of the intramedullary upright rod;
   iii. at least one anchoring element engaging with the intramedullary rod approximate the distal end; and
   iv. a vent member communicating with a supply of negative pressure.

2. A bone support device according to claim 1, wherein the vent member comprises an element having a through hole-along its longitudinal axis, said through hole engaging with a detachable suction tube.

3. A bone support device according to claim 1 wherein the proximal end of said intramedullary upright rod has a threaded opening for engaging the support element assembly.

4. A bone support device according to claim 1, wherein said support element assembly has an oblique hole extending through its longitudinal axis, for receiving therethrough a locking bolt engaging with the support element assembly.

5. A bone support device according to claim 1, wherein the device is coated with an antimicrobial agent.

* * * * *